United States Patent
Zeller

(10) Patent No.: US 12,385,991 B2
(45) Date of Patent: Aug. 12, 2025

(54) METHOD FOR CORRECTING A MAGNETIC RESONANCE MAPPING

(71) Applicant: Siemens Healthcare GmbH, Erlangen (DE)

(72) Inventor: Mario Zeller, Erlangen (DE)

(73) Assignee: Siemens Healthineers AG, Forchheim (DE)

(*) Notice: Subject to any disclaimer, the term of this patent is extended or adjusted under 35 U.S.C. 154(b) by 164 days.

(21) Appl. No.: 18/197,706

(22) Filed: May 15, 2023

(65) Prior Publication Data

US 2023/0366957 A1 Nov. 16, 2023

(30) Foreign Application Priority Data

May 16, 2022 (DE) ...................... 10 2022 204 796.6

(51) Int. Cl.
*G01V 3/00* (2006.01)
*G01R 33/24* (2006.01)
(Continued)

(52) U.S. Cl.
CPC ......... *G01R 33/243* (2013.01); *G01R 33/481* (2013.01); *G01R 33/4816* (2013.01);
(Continued)

(58) Field of Classification Search
CPC .............. G01R 33/243; G01R 33/481; G01R 33/4816; G01R 33/4828; G01R 33/5617; G01R 33/56563
(Continued)

(56) References Cited

U.S. PATENT DOCUMENTS

2008/0107229 A1* 5/2008 Thomas ................. A61B 6/037
378/207
2008/0258725 A1 10/2008 Hetherington et al.
(Continued)

FOREIGN PATENT DOCUMENTS

| CN | 105263407 A | * | 1/2016 | ........... A61B 5/0035 |
| DE | 102014201207 A1 | | 8/2015 | |
| EP | 3702800 A1 | * | 9/2020 | ......... G01R 33/4828 |

OTHER PUBLICATIONS

KR 102097396 B1 (Hong) (Year: 2020).*
(Continued)

*Primary Examiner* — Walter L Lindsay, Jr.
*Assistant Examiner* — Frederick Wenderoth
(74) *Attorney, Agent, or Firm* — Lempia Summerfield Katz LLC

(57) ABSTRACT

According to a method, first magnetic resonance signals are captured at a first time point. Second magnetic resonance signals are captured at a second time point. The first magnetic resonance signals are provoked by nuclear spin excitations of fat and water in an examination object. The second magnetic resonance signals are provoked by nuclear spin excitations of fat and water in the examination object. The nuclear spin excitations of fat and water are in phase at the first time point. The nuclear spin excitations of fat and water are in opposed phase at the second time point. A $B_0$ field map is determined based on the first magnetic resonance signals and the second magnetic resonance signals. Further magnetic resonance signals are captured. At least one magnetic resonance mapping is determined by reconstructing the further magnetic resonance signals. The at least one magnetic resonance mapping is corrected based on the $B_0$ field map.

18 Claims, 2 Drawing Sheets

(51) Int. Cl.
*G01R 33/48* (2006.01)
*G01R 33/561* (2006.01)
*G01R 33/565* (2006.01)

(52) U.S. Cl.
CPC ..... *G01R 33/4828* (2013.01); *G01R 33/5617* (2013.01); *G01R 33/56563* (2013.01)

(58) Field of Classification Search
USPC .......................................................... 324/309
See application file for complete search history.

(56) References Cited

U.S. PATENT DOCUMENTS

| | | | |
|---|---|---|---|
| 2013/0208969 A1* | 8/2013 | Bashir | G06T 7/0014 |
| | | | 382/131 |
| 2015/0204955 A1 | 7/2015 | Gumbrecht et al. | |
| 2015/0285890 A1* | 10/2015 | Bachschmidt | G01R 33/56536 |
| | | | 324/309 |
| 2016/0071263 A1* | 3/2016 | Thiruvenkadam | A61B 5/055 |
| | | | 382/131 |

OTHER PUBLICATIONS

Hernando, Diego, et al. "Robust water/fat separation in the presence of large field inhomogeneities using a graph cut algorithm." Magnetic Resonance in Medicine: An Official Journal of the International Society for Magnetic Resonance in Medicine 63.1 (2010): 79-90.

* cited by examiner

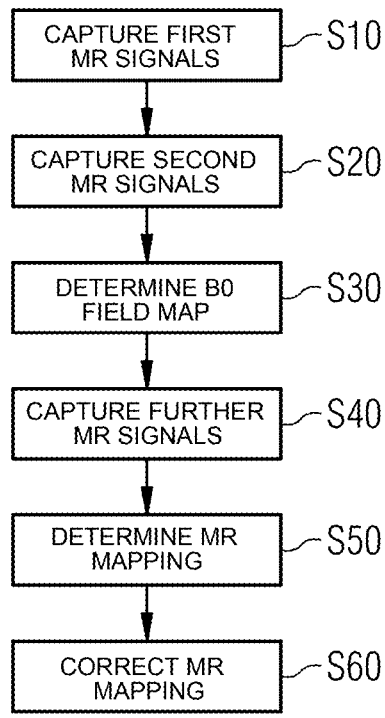
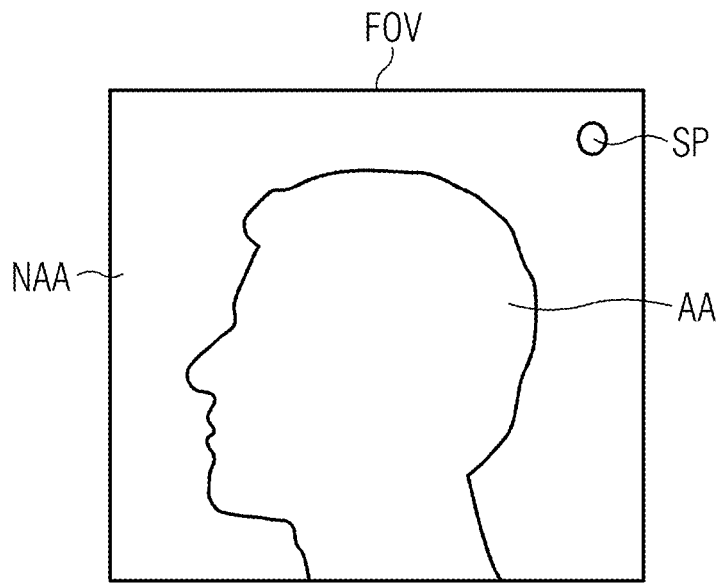

METHOD FOR CORRECTING A MAGNETIC RESONANCE MAPPING

This application claims the benefit of German Patent Application No. DE 10 2022 204 796.6, filed on May 16, 2022, which is hereby incorporated by reference in its entirety.

BACKGROUND

The present embodiments relate to a method for correcting a magnetic resonance mapping, a magnetic resonance device, an MR PET device, and a computer program product.

In the field of medical technology, imaging using magnetic resonance (MR), also referred to as magnetic resonance tomography (MRT) or magnetic resonance imaging (MRI), is characterized by high soft tissue contrasts. Using a magnetic resonance device in this context, radio frequency (RF) pulses for the purpose of generating an RF field (e.g., a $B_1$ field) and gradient pulses for the purpose of generating a magnetic field gradient are directed into an examination region in which an examination object is situated. The examination object may be a patient, for example. This triggers spatially encoded echo signals, often referred to as magnetic resonance signals, in the examination object. The magnetic resonance signals are received by the magnetic resonance device as measured data and used for the purpose of reconstructing magnetic resonance mappings.

A strong static main magnetic field, the $B_0$ field, is also generated in the examination region. In reality, the $B_0$ field often includes inhomogeneities, such that the actual resonant frequency deviates from a desired resonant frequency. The inhomogeneities may result in artifacts in the reconstructed magnetic resonance mappings.

SUMMARY AND DESCRIPTION

The scope of the present invention is defined solely by the appended claims and is not affected to any degree by the statements within this summary.

The present embodiments may obviate one or more of the drawbacks or limitations in the related art. For example, negative effects of inhomogeneities of the $B_0$ field may be reduced.

A method for correcting at least one magnetic resonance mapping is provided and includes aspects as follows. First magnetic resonance signals and second magnetic resonance signals are captured. The first magnetic resonance signals are provoked by nuclear spin excitations of fat and water in an examination object. The second magnetic resonance signals are provoked by nuclear spin excitations of fat and water in the examination object. The nuclear spin excitations of fat and water are in phase during the capture of the first magnetic resonance signals (e.g., when capturing the first magnetic resonance signals). The nuclear spin excitations of fat and water are in opposed phase during the capture of the second magnetic resonance signals (e.g., when capturing the second magnetic resonance signals). A $B_0$ field map is determined based on the first magnetic resonance signals and the second magnetic resonance signals. Further magnetic resonance signals are captured (e.g., before and/or after the capture of the first magnetic resonance signals and/or the second magnetic resonance signals). The further magnetic resonance signals are, for example, different magnetic resonance signals than the first magnetic resonance signals and/or the second magnetic resonance signals. At least one magnetic resonance mapping is determined by reconstructing the further magnetic resonance signals. The at least one magnetic resonance mapping is corrected based on the $B_0$ field map.

In this way, a $B_0$ field map (e.g., a $B_0$ map) may be created in a time-saving manner and used to correct at least one magnetic resonance mapping.

For example, the first magnetic resonance signals are captured at a first time point. For example, the second magnetic resonance signals are captured at a second time point. The second time point is a different time point than the first time point. For example, the nuclear spin excitations of fat and water are in phase at the first time point. For example, the nuclear spin excitations of fat and water are in opposed phase at the second time point. For example, the further magnetic resonance signals are captured at different time points than the first time point and the second time point.

The first time point may also be a short time period. The second time point may also be a short time period. The first time point may be, for example, a short time period in which the first magnetic resonance signals are received. The second time point may be, for example, a second time period in which the first magnetic resonance signals are received. The first time point may be, for example, a short time period in which a readout gradient is applied by a gradient coil unit of the magnetic resonance device. The second time point may be, for example, a short time period in which a readout gradient is applied by a gradient coil unit of the magnetic resonance device.

The magnetic resonance signals of a human body as an examination object originate from, for example, protons that are bound in fat and water. Due to a chemical shift, fat and water have different resonant frequencies in the same $B_0$ field. The resonant frequencies differ by approximately 3.4 ppm. When using spin-echo and/or gradient-echo sequences, for example, this results in modulation of the signal intensity as a function of the echo time TE.

A chemical shift refers, for example, to the property that the resonant frequency is shifted slightly in proportion to the field strength as a function of the type of chemical binding in which the nucleus is situated. Owing to their concentration in the human body, it is mainly hydrogen nuclei of the free water and of the fat that contribute to the image.

Immediately after beaming in an RF pulse (e.g., an excitation pulse, such as a 90° excitation pulse), the magnetization vector of the water protons and the magnetization vector of the fat protons point in the same direction. This state does not last, however, for the water protons in the homogeneous magnetic field precess faster than the fat protons by approximately 3.4 ppm, whereby the magnetization of the water protons and the fat protons disperses over time.

When the magnetization vector of the water protons and the magnetization vector of the fat protons point in the same direction, the nuclear spin excitations of water and fat are in phase (In=W+F). When the magnetization vector of the water protons and the magnetization vector of the fat protons point in opposite directions, the nuclear spin excitations of water and fat are in opposed phase (Opp=W−F).

As a result of the dispersion of the water protons and the fat protons, the in-phase relationship may occur during the capture of the first magnetic resonance signals (e.g., at the first time point), and the opposed-phase relationship may occur during the capture of the first magnetic resonance signals (e.g., at the second time point).

The echo time for the capture of the first magnetic resonance signals may be selected such that the nuclear spin excitations of fat and water are in phase. The echo time for the capture of the second magnetic resonance signals may be selected such that the nuclear spin excitations of fat and water are in opposed phase.

For example, the difference between the echo times $\Delta TE$ (e.g., the difference between the first time point and the second time point) is selected such that fat and water experience the same dephasing during this time:

$$\Delta TE = N * \frac{2\pi}{3.4 \text{ ppm} * B_{0,ref} * \gamma}$$

Here, N is a whole number, $\gamma$ is the gyromagnetic ratio, and $B_{0,ref}$ is a reference value for the field strength of the $B_0$ field.

The first time point may be a first echo time point. The first echo time point may be selected such that the nuclear spin excitations of fat and water are in phase. The second time point may be a second echo time point. The second echo time point may be selected such that the nuclear spin excitations of fat and water are in opposed phase.

In the sense of the present disclosure, "in phase" need not, however, signify an exactly identical phase relationship (e.g., the nuclear spin excitations of fat and water when capturing the first magnetic resonance signals may also be merely approximately the same). For example, the nuclear spin excitations of fat and water when capturing the first magnetic resonance signals may have a phase relationship in the range of 0°±40° (e.g., 0°±30° or 0°±20°). The magnetization vector of the water protons and the magnetization vector of the fat protons therefore need not point in exactly the same direction, but may enclose an angle of 0° to 40°, 0° to 30°, or 0° to 20°, for example.

In the sense of the present disclosure, "opposed phase" likewise need not signify an exactly opposed phase relationship (e.g., the nuclear spin excitations of fat and water when capturing the second magnetic resonance signals may also be merely approximately opposed). For example, the nuclear spin excitations of fat and water when capturing the second magnetic resonance signals may have a phase relationship in the range of 180°±40°, 180°±30°, or 180°±20°, for example. The magnetization vector of the water protons and the magnetization vector of the fat protons therefore need not point in exactly the opposite direction, but may enclose an angle of 140° to 180°, 150° to 180°, or 160° to 180°, for example.

For example, the in-phase relationship and/or the opposed-phase relationship may deviate from an exactly identical phase relationship or an exactly opposed phase relationship. This deviation may be provided and taken into account when determining the $B_0$ field map.

For example, if an expected phase difference between fat and water is supplied to a Dixon algorithm for the respective echo, a separation may be effected by the Dixon algorithm.

In a low field strength of the main magnetic field, the difference between the respective phase relationships of the first magnetic resonance signals and the second magnetic resonance signals is less than 180° (e.g., 30° and 150°, such that a difference of 150°−30°=120° is produced). The method may be accelerated thereby.

In a high field strength of the main magnetic field, the difference between the respective phase relationships of the first magnetic resonance signals and the second magnetic resonance signals is greater than 180° (e.g., 0° and 210°, such that a difference of 210°−0°=210° is produced). More time may thereby be available for data acquisition.

The first magnetic resonance signals and the second magnetic resonance signals may be used as a basis for determining a water image and/or a fat image. The determination of the $B_0$ field map takes place in the context of determining the water image and/or the fat image.

Under ideal conditions (e.g., if the $B_0$ field was absolutely homogeneous), an addition or subtraction of the magnetic resonance mappings produced from the first magnetic resonance signals and the second magnetic resonance signals magnetic resonance signals would yield images that contained, respectively, only water fractions or fat fractions of the tissue of the examination object. The magnetic resonance mapping produced from the first magnetic resonance signals may then be described by In=(W+F); the magnetic resonance mapping produced from the second magnetic resonance signals may then be described by Opp=(W−F). This would give W=½(In+Opp) for the water image and F=½(In−Opp) for the fat image accordingly.

In practice, the aforementioned spatial deviations of the $B_0$ field, for example, result in the additional phase evolution explained above. This may be described, for example, as follows: In=(W+F) and Opp=(W−F)$e^{i\Phi B}$. In this context, $\Phi B$ represents the additional phase evolutions provoked by the inhomogeneities of the $B_0$ field. In order now to determine a water image and/or a fat image, the $B_0$ field map is also to be specified. An exemplary method for specifying a background phase or a $B_0$ field map from in-phase images and opposed-phase images is proposed in Hernando, D., Kellman, P., Haldar, J. P. and Liang, Z.-P. (2010), "Robust water/fat separation in the presence of large field inhomogeneities using a graph cut algorithm," Magn. Reson. Med., 63: 79-90, https://doi.org/10.1002/mrm.22177.

The first magnetic resonance signals and the second magnetic resonance signals may be recorded by a Dixon sequence. For example, the first magnetic resonance signals and the second magnetic resonance signals are recorded by a two-dimensional or three-dimensional Dixon sequence. For example, the first magnetic resonance signals and the second magnetic resonance signals are recorded by a VIBE Dixon sequence. ("VIBE" signifies "Volumetric Interpolated Breath-hold Examination" in this context.) The VIBE Dixon sequence allows particularly rapid recording of the first magnetic resonance signals and the second magnetic resonance signals.

For example, in the case of a VIBE Dixon sequence, the first magnetic resonance signals and the second magnetic resonance signals are captured in an interleaved manner. For example: a k-space row of second magnetic resonance signals (Opp) is recorded first; a further k-space row of first magnetic resonance signals (In) is then recorded; a further k-space row of second magnetic resonance signals (Opp) is then recorded; a further k-space row of first magnetic resonance signals (In) is then recorded; etc.

The correction of the at least one magnetic resonance mapping may include a geometric distortion correction using the $B_0$ field map.

The geometric distortion correction includes, for example, a pixel displacement based on the $B_0$ field map. For example, an original pixel of an uncorrected magnetic resonance mapping is assigned a displaced pixel of a corrected magnetic resonance mapping based on the $B_0$ field map. A spatial correction may be achieved thereby.

The correction of the at least one magnetic resonance mapping may include specifying a mask of an anatomical region of the examination object based on the water image and/or the fat image. The correction of the at least one magnetic resonance mapping is then effected using the mask.

The mask may describe a region of the at least one magnetic resonance mapping, in which the at least one magnetic resonance mapping contains information (e.g., anatomical information) relating to the examination object. The mask may include a region with a plurality of pixels of the at least one magnetic resonance mapping. The correction of the at least one magnetic resonance mapping may take place solely for that region of the mask in which the at least one magnetic resonance mapping contains information (e.g., anatomical information) relating to the examination object.

The mask may be specified so as to be neither too small nor too big, in order to provide that no uncorrected regions are left "in the space" and that no "noise pixels" are displaced into the anatomy.

For the purpose of specifying the mask, use may be made of a region-growing method. In this case, a seed point may be placed at an edge of a field of view (FOV) that will be covered by the captured magnetic resonance signals (e.g., the first magnetic resonance signals and/or the second magnetic resonance signals). For example, the seed point is placed at an edge of the water image and/or of the fat image.

Starting from the seed point, the region in which the at least one magnetic resonance mapping contains or should contain no information (e.g., anatomical information) relating to the examination object (e.g., instead containing only "noise pixels") may be specified.

The region starting from and/or including the seed point (e.g., that region in which the at least one magnetic resonance mapping contains or should contain no information, such as anatomical information, relating to the examination object) may be inverted for the purpose of specifying the mask.

The capture of the further magnetic resonance signals may take place using echo planar imaging (EPI) and/or gradient echo imaging.

Echo planar imaging (e.g., an EPI sequence) is particularly susceptible to spatial $B_0$ field deviations due to the limited readout bandwidth of the echo train in a phase-encoding direction. Such field deviations result in a spatially dependent phase evolution and therefore spatially differing pixel displacements in a phase-encoding direction.

In the case of gradient echo imaging (e.g., a gradient echo sequence) using a low bandwidth, the displacement may take place in a readout direction. This displacement may also be corrected using the method proposed here.

The proposed method may be used for imaging of the brain. $B_0$ field deviations otherwise result in particularly strong image artifacts here.

According to a further embodiment of the proposed method, provision is made for the method to include the capture of positron emission tomography signals (PET signals). The method includes the capture of measured data for correcting the attenuation of the positron emission tomography signals. The capture of measured data for correcting the attenuation of the positron emission tomography signals includes the capture of the first magnetic resonance signals and of the second magnetic resonance signals. The measured data for attenuation correction and the first magnetic resonance signals and the second magnetic resonance signals may be captured together.

The PET signals and the magnetic resonance signals may be captured using an MR PET system. The proposed method may be an MR PET method. The measured data for attenuation correction may be suitable for calculating tissue-specific attenuation coefficients for a PET reconstruction. It is thereby possible to differentiate between normal tissue, air, bones, fat, etc.

The capture of measured data for correcting the attenuation of the PET signals may take place before the capture of the PET signals and/or before the capture of the further magnetic resonance signals (e.g., in the context of a prescan). The first magnetic resonance signals and/or the second magnetic resonance signals may also be captured in the context of the prescan.

The capture of measured data for correcting the attenuation of the PET signals, the capture of the first magnetic resonance signals, and/or the capture of the second magnetic resonance signals may take place simultaneously and/or in parallel. The capture of the measured data for correcting the attenuation of the PET signals, the capture of the first magnetic resonance signals, and/or the capture of the second magnetic resonance signals may be effected by a Dixon sequence (e.g., the same Dixon sequence). The measured data for correcting the attenuation of the PET signals, the first magnetic resonance signals, and the second magnetic resonance signals may be captured using just one prescan. It is thereby possible to economize measurement time.

For example, the capture of the measured data for correcting the attenuation of the PET signals includes capturing measured data by a sequence with an ultra-short echo time, UTE measured data. In this case, the correction of the at least one magnetic resonance mapping includes specifying a mask of an anatomical region of the examination object using the UTE measured data, where the correction of the at least one magnetic resonance mapping is effected using the mask.

It is advantageous that the UTE measured data is particularly suitable for specifying a mask because the UTE measured data allows bones to be represented in particularly rich contrast due to its short echo time TE.

A sequence with an ultra-short echo time (UTE sequence) in the sense of the present application may be, for example, a sequence with an echo time TE of less than 500 μs (e.g., less than 100 μs). For example, the minimum nominal echo time is between 8 and 100 μs. For example, a PETRA sequence (Pointwise Encoding Time reduction with Radial Acquisition) is highly suitable for mask specification due to its short echo time TE.

For example, the capture of measured data for correcting the attenuation of the PET signals includes a combination of capturing measured data using a sequence having an ultra-short echo time and a Dixon sequence.

Further proposed is a magnetic resonance device or an MR PET device that is configured to execute a method as described above. Such a magnetic resonance device includes, for example, a radio frequency antenna unit for capturing magnetic resonance signals and/or a system control unit for determining the $B_0$ field map and/or for determining the at least one magnetic resonance mapping and/or for correcting the at least one magnetic resonance mapping. The system control unit may include one or more processors and/or one or more memory modules. Such an MR PET device also includes, for example, a detector unit for capturing PET signals.

The advantages of the magnetic resonance device or the MR PET device correspond substantially to the advantages of the method of the present embodiments for correcting at least one magnetic resonance mapping. The advantages are explained in detail above. Features, advantages, or alternative embodiment variants cited in this context may likewise be applied to the computer program product described below, and vice versa.

Further proposed is a computer program product that includes a program and may be loaded directly into a memory of a programmable system control unit of a magnetic resonance device or MR PET device and has program means (e.g., libraries and help functions) for executing a method according to the present embodiments for correcting at least one magnetic resonance mapping when the computer program product is executed in the system control unit. In this case, the computer program product may include software with source code that has yet to be compiled and linked or merely needs to be interpreted, or executable software code that merely needs to be loaded into the system control unit in order to execute. By virtue of the computer program product, the method of the present embodiments may be executed in a manner that is fast, resilient, and allows identical repetition. The computer program product is configured, such that the computer program product may use the system control unit to execute method acts according to the present embodiments.

In this case, the system control unit may have the relevant prerequisites such as, for example, corresponding working memory, a corresponding graphics card or a corresponding logic unit, such that the respective method acts may be executed efficiently. The computer program product is stored, for example, on a computer-readable medium or on a network or server, from where the computer program may be loaded into the processor of a local system control unit that may be directly connected to the magnetic resonance device or configured as part of the magnetic resonance device or MR PET device.

Further, control information of the computer program product may be stored on an electronically readable data medium (e.g., a non-transitory computer-readable storage medium). The control information of the electronically readable data medium may be configured such that the control information performs a method according to the present embodiments when the data medium is used in a system control unit of a magnetic resonance device or MR PET device. Examples of electronically readable data media include a DVD, magnetic tape, or a USB stick, on which electronically readable control information (e.g., software) is stored. When this control information is read from the data medium and stored in a system control unit of the magnetic resonance device or MR PET device, it is possible to perform all of the embodiment variants of the method of the present embodiments described above. The present embodiments may therefore also relate to the cited computer-readable medium and/or the cited electronically readable data medium.

BRIEF DESCRIPTION OF THE DRAWINGS

Further advantages, features, and details of the invention are derived from the embodiments described below and with reference to the drawings. Mutually corresponding parts are denoted by the same reference signs in all figures, in which:

FIG. 2 shows a flow diagram of one embodiment of a method for correcting at least one magnetic resonance mapping; and FIG. 3 shows an example schematic image for specifying a mask.

DETAILED DESCRIPTION

Figure 1:
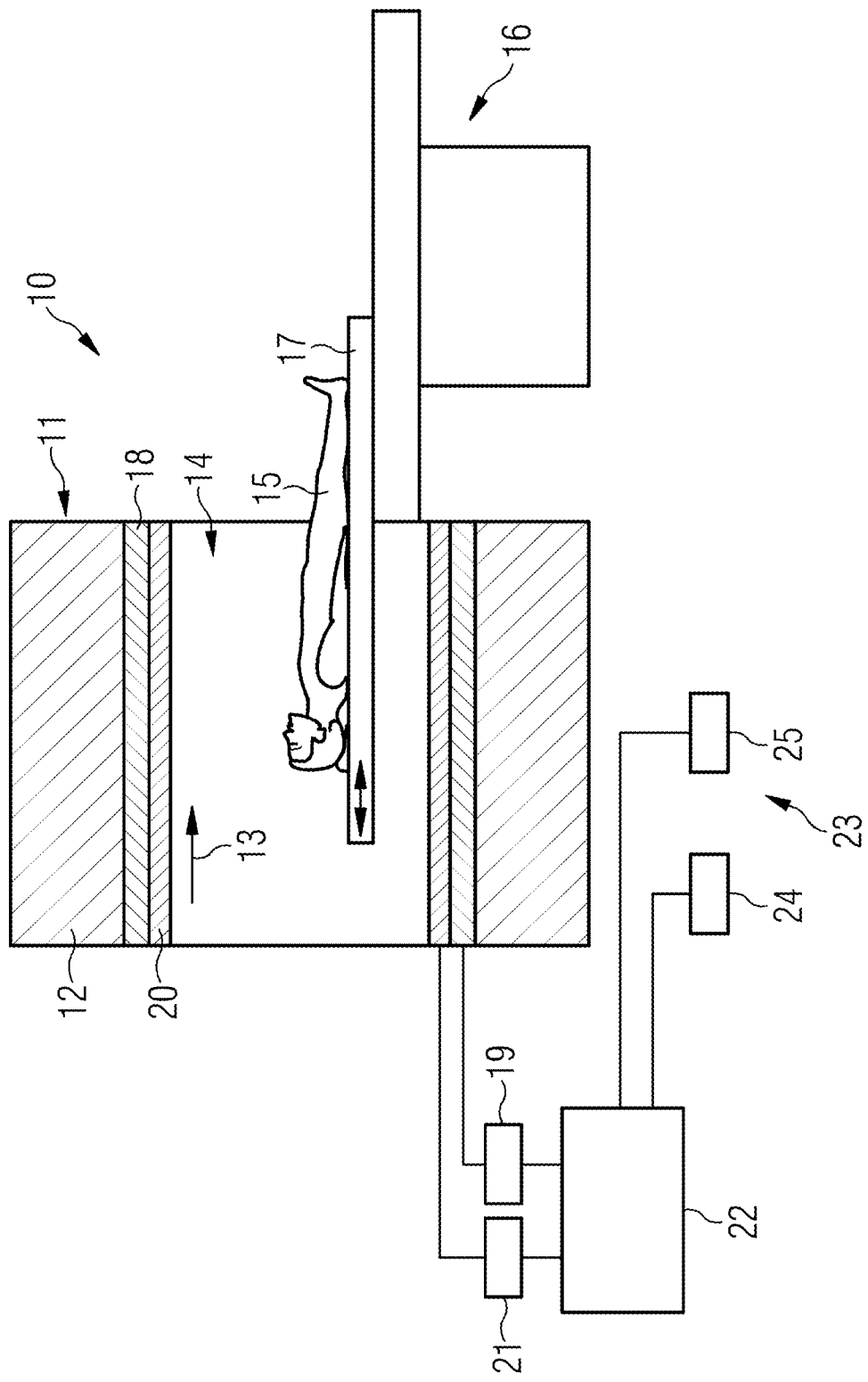
FIG. 1 shows one embodiment of a magnetic resonance device in a schematic representation.

FIG. 1 schematically represents one embodiment of a magnetic resonance device 10. The magnetic resonance device 10 includes a magnet unit 11 having a main magnet 12 for generating a strong and, for example, temporally constant main magnetic field 13. The magnetic resonance device 10 further includes a patient receiving region 14 for receiving a patient 15. The patient receiving region 14 in the present exemplary embodiment is cylindrical and is circumferentially surrounded in a cylindrical manner by the magnet unit 11. However, a different design of the patient receiving region 14 may be provided. The patient 15 may be pushed into the patient receiving region 14 by a patient support device 16 of the magnetic resonance device 10. For this purpose, the patient support device 16 has a patient couch 17 that is embodied so as to be mobile within the patient receiving region 14.

The magnet unit 11 also has a gradient coil unit 18 for generating magnetic field gradients that are used for spatial encoding during imaging. The gradient coil unit 18 is controlled by a gradient control unit 19 of the magnetic resonance device 10. The magnet unit 11 also includes a radio frequency antenna unit 20 that, in the present exemplary embodiment, is configured as a body coil that is permanently integrated in the magnetic resonance device 10. The radiofrequency antenna unit 20 is controlled by a radio frequency antenna control unit 21 of the magnetic resonance device 10 and beams radio frequency magnetic resonance sequences into an examination volume that is essentially formed by a patient receiving region 14 of the magnetic resonance device 10. An excitation of atomic nuclei occurs as a result of the main magnetic field 13 that is generated by the main magnet 12. Magnetic resonance signals are generated by relaxation of the excited atomic nuclei. The radio frequency antenna unit 20 is configured to receive the magnetic resonance signals.

The magnetic resonance device 10 has a system control unit 22 for controlling the main magnet 12, the gradient control unit 19, and the radio frequency antenna control unit 21. The system control unit 22 controls the magnetic resonance device 10 centrally, for example, performing a predefined imaging EPI sequence. The system control unit 22 further includes an evaluation unit (not shown) for evaluating the magnetic resonance signals that are captured during the magnetic resonance examination. Further, the magnetic resonance device 10 includes a user interface 23 that is connected to the system control unit 22. Control information such as imaging parameters, for example, and reconstructed magnetic resonance mappings may be displayed on a display unit 24 (e.g., at least one monitor) of the user interface 23 for medical operating staff. The user interface 23 also has an input unit 25 by which information and/or parameters may be entered by the medical operating staff during a measuring operation.

The magnetic resonance device 10 may also include a PET device (not shown), such that this combined device may also be referred to as an MR PET device. Such a PET device may include, for example, a plurality of positron emission tomography detector modules (PET detector modules 22) that are arranged in the form of a ring and surround the patient receiving region 14 circumferentially. The PET detector modules may be arranged, for example, between the radio frequency antenna unit 20 and the gradient coil unit 18 of the magnetic resonance device 10 and therefore integrated in the magnetic resonance device 10 with significant space savings.

The PET detector modules each have a plurality of positron emission tomography detector elements (PET detector elements) (not shown) that are arranged to form a PET detector array. The PET detector array includes a scintillation detector array with scintillation crystals (e.g., LSO crystals). Each of the PET detector modules may also include a photo diode array (e.g., an avalanche photo diode array or APD photo diode array) arranged downstream of the scintillation detector array within the PET detector modules. The PET detector array also has detector electronics (not shown) including an electrical amplifier circuit and further electronic components (not shown). For the purpose of controlling the PET detector modules, the PET device has a control unit that may be integrated in the system control unit 22, for example.

The PET detector modules are used to capture photon pairs resulting from the annihilation of a positron with an electron. Trajectories of the two photons enclose an angle of 180°. In addition, the two photons each have an energy of 511 keV. The positron is emitted by a radio pharmacon in this case, the radio pharmacon being administered to the patient 15 by injection. When passing through matter, the photons resulting from the annihilation may be absorbed, the absorption probability being dependent on the path length through the matter and the corresponding absorption coefficient of the matter. When evaluating positron emission tomography signals (PET signals), attenuation correction of these signals relating to the attenuation caused by components situated in the beam path is therefore advantageous.

The magnetic resonance device 10 is configured to execute a method as per FIG. 2. In S10, first magnetic resonance signals are captured (e.g., at a first time point) via, for example, the radio frequency antenna unit 20 of the magnetic resonance device 10. In S20, second magnetic resonance signals are captured (e.g., at a second time point) via, for example, the radio frequency antenna unit 20 of the magnetic resonance device 10. The first magnetic resonance signals and the second magnetic resonance signals are provoked in each case by nuclear spin excitations of fat and water in the patient 15. In this case, the nuclear spin excitations of fat and water are in phase (e.g., approximately in phase) during the capture of the first magnetic resonance signals and are in opposed phase (e.g., approximately opposed phase) during the capture of the second magnetic resonance signals. In S30, a $B_0$ field map is determined based on the first magnetic resonance signals and the second magnetic resonance signals (e.g., by the system control unit 22 of the magnetic resonance device 10). In S40, further magnetic resonance signals are captured (e.g., via the radio frequency antenna unit 20 of the magnetic resonance device 10). In S50, at least one magnetic resonance mapping is determined by reconstructing the further magnetic resonance signals (e.g., by the system control unit 22 of the magnetic resonance device 10). In S60, the at least one magnetic resonance mapping is corrected based on the $B_0$ field map (e.g., by the system control unit 22 of the magnetic resonance device 10).

According to the prior art, at present, the specification of a $B_0$ field map is normally based on an isotropically recorded 2D gradient echo sequence with three echoes. Using a suitable selection of the echo times, this allows the avoidance of phase jumps (e.g., phase wraps) when specifying the field map from the image phase of the three echoes. However, if spin types having different Larmor frequencies are present (e.g., usually fat and water), erroneous specification of the field deviation occurs in regions in which the number of fat spins is greater than the number of water spins. The recording of such a gradient echo sequence, for example, covering the entire head of the patient 15, would also be considerably time-consuming.

According to an embodiment variant of the proposed method, capture of the first magnetic resonance signals and the second magnetic resonance signals in S10 and S20, respectively, may be achieved, for example, by a Dixon sequence (e.g., a two-dimensional or three-dimensional Dixon sequence, such as a TSE sequence or VIBE Dixon sequence).

In the case of DIXON imaging, measured data is usually recorded at at least two time points. The first echo time point is selected such that fat spins and water spins are in phase at that time (In=W+F), and are oriented in opposed phase at the second time point (Opp=W−F). Under ideal conditions, addition or subtraction of the two data sets would then result in images containing respectively either only water or only fat fractions of the tissue. In practice, the aforementioned spatial deviations of the $B_0$ field, for example, result in an additional phase evolution, and therefore this simple approach is inadequate.

According to the prior art, the background phase or $B_0$ field map is intended merely for the purpose of correctly separating water and fat fractions, and is then discarded. In the present embodiments, Dixon imaging may be performed for the explicit purpose of specifying the $B_0$ field map, and the $B_0$ field map may then be used for the purpose of correcting the at least one magnetic resonance mapping.

The capture of the first magnetic resonance signals in S10, the second magnetic resonance signals in S20, and/or further magnetic resonance signals in S40 may be achieved, for example, by echo planar imaging (e.g., an EPI sequence).

Echo planar imaging is susceptible to spatial $B_0$ field deviations due to the limited readout bandwidth of the echo train in a phase-encoding direction. Such field deviations are caused, for example, by susceptibility jumps at boundary surfaces between water and air and result in a spatially dependent phase evolution. Without the correction provided in the present embodiments, this would result in spatially differing pixel displacements in a phase-encoding direction, which would be manifested in stretching or compressing of the image depending on the operational sign. Since the effects are particularly pronounced in the context of brain imaging, use of the proposed method is particularly effective here.

In S30, a water image and/or a fat image may be determined based on the first magnetic resonance signals and the second magnetic resonance signals. For example, the determination of the $B_0$ field map takes place in the context of determining the water image and/or the fat image.

In S60, the correction of the at least one magnetic resonance mapping may include a geometric distortion correction using the $B_0$ field map.

In S60, for example, a mask of an anatomical region of the examination object may be specified based on the water image and/or the fat image. The correction of the at least one magnetic resonance mapping is effected using the mask. A region-growing method may be used for the purpose of specifying the mask. By way of example, this is explained in greater detail in the following with reference to FIG. 3: illustrated by way of example is a fat image having a specific field of view FOV that is covered by the first magnetic resonance signals and/or the second magnetic resonance signals. A head of the patient 15 as illustrated by way of example in FIG. 3 is usually surrounded entirely by subcutaneous fat. The calculated fat image may therefore also be used to reliably specify the mask for the field map. Since EPI sequences are usually performed using fat saturation, the subcutaneous fat may serve as a reliable outer boundary for masking of the field map. A seed point SP is placed at the edge of the field of view FOV (e.g., in the non-anatomical region NAA). The non-anatomical region NAA is a region of the image (e.g., of the fat image or also of a water image) that contains no anatomical information relating to the patient 15. By contrast, the anatomical region AA is a region that contains anatomical information relating to the patient 15. Using the region-growing method, it is now possible starting from the seed point SP to specify the non-anatomical region NAA that extends as far as the subcutaneous fat. It is then possible, using region inversion, to specify the anatomical region AA that corresponds to the mask. Due to the high intensity of fat, this procedure is resilient to image noise.

In addition to the anticipated greater resilience in the specification of field maps and/or masks, the higher speed of the DIXON recording is a significant advantage. A VIBE DIXON sequence with an identical resolution of 5×5×5 mm$^3$ to the three-echo gradient sequence described above requires only 8 seconds recording time at 3 T, representing a reduction by a factor of approximately 3 in comparison with conventional methods. This is due to the fact that: first, only two echoes are required; and second, the echo times are selected according to the in-phase and opposed-phase condition (e.g., 1.23 ms and 2.46 ms at 3 T), and are therefore significantly shorter than a three-echo sequence (e.g., 2.4 ms, 4.6 ms and 7.1 ms). Faster speeds than a conventional 2D recording may also be achieved using a possible 3D recording technique using CAIPIRINHA. The method may be used with a field strength of less than 2 T of the main magnetic field of the magnetic resonance device 10. For example, at 1.5 T, the sequence requires approximately 11 seconds, corresponding to an acceleration by a factor greater than 4; therefore, the method is highly advantageous at low field strengths, for example.

In S40, in addition to the capture of further magnetic resonance signals, positron emission tomography signals may also be captured. For the attenuation correction of the PET signals, use may be made of measured data that is captured during the course of capturing the first magnetic resonance signals and the second magnetic resonance signals in S10 and S20, respectively. For example, for the purpose of attenuation correction, measured data may be captured by a sequence with an ultra-short echo time, UTE measured data. A mask of an anatomical region of the examination object may be specified based on the UTE measured data, the correction of the at least one magnetic resonance mapping in S60 being effected using the mask.

In conclusion, both the methods described in detail above and the illustrated capture specimen generating unit and magnetic resonance device are merely examples of embodiments that may be modified in all manner of ways by a person skilled in the art without thereby departing from the scope of the invention. Further, the use of the indefinite article "a" or "an" does not preclude multiple instances of the features concerned. Likewise, the term "unit" does not preclude the relevant component consisting of a plurality of interacting sub-components, which may also be spatially distributed if applicable.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for correcting at least one magnetic resonance mapping, the method comprising:
   capturing first magnetic resonance signals;
   capturing second magnetic resonance signals, wherein the first magnetic resonance signals and the second magnetic resonance signals are provoked in each case by nuclear spin excitations of fat and water in an examination object, wherein the nuclear spin excitations of fat and water are in phase during the capturing of the first magnetic resonance signals, and
   wherein the nuclear spin excitations of fat and water are in opposed phase during the capturing of the second magnetic resonance signals;
   determining a $B_0$ field map based on the first magnetic resonance signals and the second magnetic resonance signals;
   capturing further magnetic resonance signals;
   determining the at least one magnetic resonance mapping, the determining of the at least one magnetic resonance mapping comprising reconstructing the further magnetic resonance signals; and
   correcting the at least one magnetic resonance mapping based on the $B_0$ field map.

2. A magnetic resonance device configured to:
   capture first magnetic resonance signals;
   capture second magnetic resonance signals, wherein the first magnetic resonance signals and the second magnetic resonance signals are provoked in each case by nuclear spin excitations of fat and water in an examination object, wherein the nuclear spin excitations of fat and water are in phase during the capturing of the first magnetic resonance signals, and
   wherein the nuclear spin excitations of fat and water are in opposed phase during the capturing of the second magnetic resonance signals;
   determine a $B_0$ field map based on the first magnetic resonance signal and the second magnetic resonance signal;
   capture further magnetic resonance signals;
   determine the at least one magnetic resonance mapping, the determining of the at least one magnetic resonance mapping comprising reconstructing the further magnetic resonance signals; and
   correct the at least one magnetic resonance mapping based on the $B_0$ field map.

3. A magnetic resonance (MR) positron emission tomography (PET) device that is configured to:
   capture first magnetic resonance signals;
   capture second magnetic resonance signals, wherein the first magnetic resonance signals and the second magnetic resonance signals are provoked in each case by nuclear spin excitations of fat and water in an examination object, wherein the nuclear spin excitations of fat and water are in phase during the capturing of the first magnetic resonance signals, and
wherein the nuclear spin excitations of fat and water are in opposed phase during the capturing of the second magnetic resonance signals;
determine a $B_0$ field map based on the first magnetic resonance signals and the second magnetic resonance signals;
capture further magnetic resonance signals;
determine the at least one magnetic resonance mapping, the determination of the at least one magnetic resonance mapping comprising reconstruction of the further magnetic resonance signals;
correct the at least one magnetic resonance mapping based on the $B_0$ field map;
capture positron emission tomography signals; and
capture measured data for correction of attenuation of the positron emission tomography signals,
wherein the capture of the measured data for correction of the attenuation of the positron emission tomography signals comprises capture of the first magnetic resonance signals and the second magnetic resonance signals.

4. The method of claim 1, further comprising determining a water image, a fat image, or the water image and the fat image based on the first magnetic resonance signals and the second magnetic resonance signals,
wherein the determining of the $B_0$ field map takes place in the context of determining the water image, the fat image, or the water image and the fat image.

5. The method of claim 1, wherein the first magnetic resonance signals and the second magnetic resonance signals are recorded by a Dixon sequence.

6. The method of claim 1, wherein the correcting of the at least one magnetic resonance mapping comprises geometric distortion correcting using the $B_0$ field map.

7. The method of claim 1, further comprising:
capturing positron emission tomography signals; and
capturing measured data for correcting attenuation of the positron emission tomography signals,
wherein capturing the measured data for correcting the attenuation of the positron emission tomography signals comprises capturing the first magnetic resonance signals and the second magnetic resonance signals.

8. The MR PET device of claim 3, wherein the MR PET device has a field strength of a main magnetic field of less than 2 T.

9. The magnetic resonance device of claim 2, wherein the magnetic resonance device has a field strength of a main magnetic field of less than 2 T.

10. The method of claim 1, wherein the further magnetic resonance signals are captured before, or before and after the capturing of the first magnetic resonance signals and the second magnetic resonance signals.

11. The method of claim 4, further comprising specifying a mask of an anatomical region of the examination object based on the water image, the fat image, or the water image and the fat image,
wherein the correcting of the at least one magnetic resonance mapping is effected using the mask.

12. The method of claim 5, wherein the first magnetic resonance signals and the second magnetic resonance signals are recorded by a two-dimensional or three-dimensional Dixon sequence.

13. The method of claim 5, wherein the first magnetic resonance signals and the second magnetic resonance signals are recorded by a TSE sequence or a VIBE Dixon sequence.

14. The method of claim 7, wherein capturing the measured data for correcting the attenuation comprises capturing the measured data using a sequence with an ultra-short echo time, UTE-measured data,
wherein the method further comprises specifying a mask of an anatomical region of the examination object using the UTE-measured data, and
wherein the correcting of the at least one magnetic resonance mapping is effected using the mask.

15. The method of claim 7, wherein the positron emission tomography signals, the first magnetic resonance signals, and the second magnetic resonance signals are all captured simultaneously or with a single pre-scan.

16. The method of claim 11, wherein a region-growing method is used for the specifying of the mask.

17. The method of claim 16, wherein a seed point is placed at an edge of a field of view that is covered by the first second magnetic resonance signals, the second magnetic resonance signals, or the first magnetic resonance signals and the second magnetic resonance signals.

18. The method of claim 14, wherein the ultra-short echo time is less than 400 µs.

* * * * *